(12) United States Patent
Kim et al.

(10) Patent No.: US 8,652,446 B2
(45) Date of Patent: *Feb. 18, 2014

(54) APPARATUS AND METHOD FOR WHITENING TEETH

(75) Inventors: Ji-Young Kim, Daejeon (KR); Jong-Ho Kim, Daejeon (KR); Sug-Youn Chang, Daejeon (KR); Sei-Young Yun, Seoul (KR); Hae-Young Yang, Daejeon (KR); Sang-Hoon Kwak, Daejeon (KR)

(73) Assignee: LG Household & Healthcare Ltd., Seoul (KR)

( * ) Notice: Subject to any disclaimer, the term of this patent is extended or adjusted under 35 U.S.C. 154(b) by 1938 days.

This patent is subject to a terminal disclaimer.

(21) Appl. No.: 10/717,226

(22) Filed: Nov. 19, 2003

(65) Prior Publication Data

US 2004/0136927 A1    Jul. 15, 2004

Related U.S. Application Data

(63) Continuation-in-part of application No. 10/243,182, filed on Sep. 13, 2002, now Pat. No. 6,689,344, which is a continuation-in-part of application No. 10/049,817, filed as application No. PCT/KR01/00207 on Feb. 13, 2001, now Pat. No. 6,682,721.

(60) Provisional application No. 60/324,555, filed on Sep. 25, 2001.

(30) Foreign Application Priority Data

Mar. 17, 2000 (KR) .................................. 2000-13636
Dec. 8, 2000 (KR) .................................. 2000-74599
Nov. 21, 2002 (KR) ......................... 10-2002-0072603
Jul. 28, 2003 (KR) ......................... 10-2003-0051912

(51) Int. Cl.
*A61Q 11/00* (2006.01)
*A61K 8/22* (2006.01)

(52) U.S. Cl.
USPC .................. 424/53; 424/49; 424/57; 433/216

(58) Field of Classification Search
USPC ............................ 424/53, 49; 433/216, 217.1
See application file for complete search history.

(56) References Cited

U.S. PATENT DOCUMENTS

| | | | |
|---|---|---|---|
| 4,517,173 A | 5/1985 | Kizawa et al. | |
| 4,696,757 A | 9/1987 | Blank et al. | |
| 4,713,243 A | 12/1987 | Schiraldi et al. | |
| 4,728,291 A | 3/1988 | Golub | |
| 4,741,700 A | 5/1988 | Barabe | |
| 4,741,941 A | 5/1988 | Englebert et al. | |
| 4,786,253 A | 11/1988 | Morais | |
| 4,799,888 A | 1/1989 | Golub | |
| 4,812,308 A | 3/1989 | Winston et al. | |
| 4,839,156 A | 6/1989 | Ng et al. | |
| 4,839,157 A | 6/1989 | Mei-King Ng et al. | |
| RE33,093 E | 10/1989 | Schiraldi et al. | |
| 4,891,211 A | 1/1990 | Winston | |
| 4,895,721 A | 1/1990 | Drucker | |
| 4,900,552 A | 2/1990 | Sanvordeker et al. | |
| 4,900,554 A | 2/1990 | Yanagibashi et al. | |
| 4,919,615 A | 4/1990 | Croll | |
| 4,933,182 A | 6/1990 | Higashi et al. | |
| 4,940,587 A * | 7/1990 | Jenkins et al. | ................ 424/480 |
| 4,983,379 A | 1/1991 | Schaeffer | |
| 4,983,380 A | 1/1991 | Yarborough | |
| 5,000,940 A | 3/1991 | Staples et al. | |
| 5,008,106 A | 4/1991 | Merianos et al. | |
| 5,009,885 A | 4/1991 | Yarborough | |
| 5,032,178 A | 7/1991 | Cornell | |
| 5,041,280 A | 8/1991 | Smigel | |
| 5,055,287 A | 10/1991 | Kessler | |
| 5,059,417 A | 10/1991 | Williams et al. | |
| 5,084,268 A | 1/1992 | Thaler | |
| 5,098,303 A | 3/1992 | Fischer | |
| 5,110,583 A | 5/1992 | Sampathkumar | |

(Continued)

FOREIGN PATENT DOCUMENTS

| | | |
|---|---|---|
| GB | 2108841 | 5/1983 |
| JP | 10-17448 | 1/1998 |
| JP | 1017448 A1 | 1/1998 |
| JP | 10017448 | 1/1998 |
| JP | 2000-281548 | 10/2000 |
| WO | 9517158 A1 | 6/1995 |
| WO | WO95/17158 | 6/1995 |
| WO | WO 98/55044 | 3/1999 |
| WO | WO 99/62472 | 12/1999 |
| WO | WO 00/54699 | 9/2000 |
| WO | WO 0168045 | 9/2001 |

OTHER PUBLICATIONS

Supplementary European Search Report for EP 01 90 6382, (corresponding EP application for parent application PCT/KR01/00207.
Kim, et al., U.S. Appl. No. 10/445,589 entitled Patches for Whitening Teeth, 48 pp.
Chang, et al., U.S. Appl. No. 10/177,689 entitled Multi-Layer Patches for Teeth Whitening, 89 pp.
Chalykh, et al., Fracture Mechanics of Poly(N-Vinyl Pyrrolidone) Poly(Ethylene Glycl) Hyrdrogel Adhesive Joints, Polym. Mater. Sci. Eng., vol. 81, 1999, pp. 427-428.
Office Action dated Jan. 16, 2007 in U.S. Appl. No. 10/915,283.

*Primary Examiner* — Lezah Roberts
(74) *Attorney, Agent, or Firm* — Fox Rothschild LLP; Gerald P. Norton; Shahnam Sharareh

(57) ABSTRACT

Disclosed herein is a pair of dry type patches for teeth whitening, having a patch for upper teeth and a patch for lower teeth, in which the patch for upper teeth has a shape different from the patch for lower teeth, and each patch has a controlled width and shape such that the contact area of each patch with gums is minimized. In the patch for upper teeth, a central portion covering right and left upper central incisors is widest. In the patch for lower teeth, either portion covering right and left lower canine teeth is widest. Since the dry type patches covers all the portions of the teeth while minimizing the contact area with gums, no or little irritation is caused and wearability is excellent.

31 Claims, 6 Drawing Sheets

(56) References Cited

U.S. PATENT DOCUMENTS

| | | | |
|---|---|---|---|
| 5,122,365 A | 6/1992 | Murayama | |
| 5,128,122 A | 7/1992 | Cerami et al. | |
| 5,130,124 A * | 7/1992 | Merianos et al. | 424/53 |
| 5,166,233 A | 11/1992 | Kuroya et al. | |
| 5,171,564 A | 12/1992 | Nathoo et al. | |
| 5,177,113 A * | 1/1993 | Biss et al. | 514/772.5 |
| RE34,196 E | 3/1993 | Munro | |
| 5,192,532 A | 3/1993 | Guay et al. | |
| 5,208,010 A | 5/1993 | Thaler | |
| 5,217,710 A | 6/1993 | Williams et al. | |
| 5,234,342 A | 8/1993 | Fischer | |
| 5,234,957 A | 8/1993 | Mantelle | |
| 5,240,415 A | 8/1993 | Haynie | |
| 5,256,402 A | 10/1993 | Prencipe et al. | |
| 5,279,816 A | 1/1994 | Church et al. | |
| 5,281,412 A | 1/1994 | Lukacovic et al. | |
| 5,290,566 A | 3/1994 | Schow et al. | |
| 5,292,502 A | 3/1994 | Burke et al. | |
| 5,302,375 A | 4/1994 | Viscio | |
| 5,310,563 A | 5/1994 | Curtis et al. | |
| 5,326,685 A | 7/1994 | Gaglio et al. | |
| 5,332,576 A | 7/1994 | Mantelle | |
| 5,340,314 A | 8/1994 | Tarvis | |
| 5,340,581 A | 8/1994 | Tseng et al. | |
| 5,348,734 A | 9/1994 | Ratcliff | |
| 5,366,285 A | 11/1994 | Borgen et al. | |
| 5,372,802 A | 12/1994 | Barrows et al. | |
| 5,376,006 A | 12/1994 | Fischer | |
| 5,380,198 A | 1/1995 | Suhonen | |
| 5,401,495 A | 3/1995 | Murayama | |
| 5,409,631 A | 4/1995 | Fischer | |
| 5,409,703 A * | 4/1995 | McAnalley et al. | 424/435 |
| 5,425,953 A | 6/1995 | Sinitov et al. | |
| 5,437,858 A | 8/1995 | Hungerbach et al. | |
| 5,438,076 A | 8/1995 | Friedman et al. | |
| 5,505,956 A | 4/1996 | Kim et al. | |
| 5,536,285 A | 7/1996 | Isaksson et al. | |
| 5,560,379 A | 10/1996 | Pieczenik | |
| 5,565,190 A | 10/1996 | Santalucia et al. | |
| 5,575,654 A | 11/1996 | Fontenot | |
| 5,611,687 A | 3/1997 | Wagner | |
| 5,614,174 A | 3/1997 | Hsu et al. | |
| 5,620,322 A | 4/1997 | Lococo | |
| 5,626,866 A | 5/1997 | Ebert et al. | |
| 5,631,000 A | 5/1997 | Pellico et al. | |
| 5,631,055 A | 5/1997 | Vines et al. | |
| 5,639,445 A | 6/1997 | Curtis et al. | |
| 5,641,530 A * | 6/1997 | Chen | 426/532 |
| 5,648,064 A | 7/1997 | Gaffar et al. | |
| 5,683,680 A | 11/1997 | Santalucia et al. | |
| 5,689,182 A | 11/1997 | Togo et al. | |
| 5,700,478 A | 12/1997 | Biegajski et al. | |
| 5,707,611 A | 1/1998 | Ikemura et al. | |
| 5,707,736 A | 1/1998 | Levy et al. | |
| 5,713,738 A | 2/1998 | Yarborough | |
| 5,718,886 A | 2/1998 | Pellico | |
| 5,723,132 A | 3/1998 | Tseng et al. | |
| 5,725,843 A | 3/1998 | Fischer | |
| 5,746,598 A | 5/1998 | Fischer | |
| 5,766,574 A | 6/1998 | Christina-Beck et al. | |
| 5,770,105 A | 6/1998 | Fischer | |
| 5,770,182 A | 6/1998 | Fischer | |
| 5,776,437 A | 7/1998 | Burgess et al. | |
| 5,785,527 A | 7/1998 | Jensen et al. | |
| 5,785,957 A | 7/1998 | Losee et al. | |
| 5,814,303 A | 9/1998 | Williams et al. | |
| 5,814,304 A | 9/1998 | Wong et al. | |
| 5,820,822 A | 10/1998 | Kross | |
| 5,820,852 A | 10/1998 | Burgess et al. | |
| 5,820,854 A | 10/1998 | Glandorf | |
| 5,846,570 A | 12/1998 | Barrow et al. | |
| 5,849,269 A | 12/1998 | Burgess et al. | |
| 5,851,514 A | 12/1998 | Hassan et al. | |
| 5,855,875 A | 1/1999 | Williams et al. | |
| 5,858,332 A | 1/1999 | Jensen et al. | |
| 5,863,202 A | 1/1999 | Fontenot et al. | |
| 5,879,691 A | 3/1999 | Sagel et al. | |
| 5,885,553 A | 3/1999 | Michael | |
| 5,885,554 A | 3/1999 | Michael et al. | |
| 5,891,453 A | 4/1999 | Sagel et al. | |
| 5,894,017 A | 4/1999 | Sagel et al. | |
| 5,902,568 A | 5/1999 | Ryles et al. | |
| 5,908,614 A | 6/1999 | Montgomery | |
| 5,914,118 A | 6/1999 | Yamamura et al. | |
| 5,915,969 A | 6/1999 | Linden | |
| 5,922,307 A | 7/1999 | Montgomery | |
| 5,928,628 A | 7/1999 | Pellico | |
| 5,932,193 A | 8/1999 | Lopez et al. | |
| 5,945,032 A * | 8/1999 | Breitenbach et al. | 252/186.29 |
| 5,980,249 A | 11/1999 | Fontenot | |
| 5,985,249 A | 11/1999 | Fischer | |
| 5,989,526 A | 11/1999 | Aaslyng et al. | |
| 5,989,569 A | 11/1999 | Dirksing et al. | |
| 6,007,795 A | 12/1999 | Masterman et al. | |
| 6,017,515 A | 1/2000 | van den Bosch | |
| 6,022,528 A | 2/2000 | Waterfield et al. | |
| 6,030,222 A | 2/2000 | Tarver | |
| 6,036,249 A | 3/2000 | Kuntz | |
| 6,036,943 A | 3/2000 | Fischer | |
| 6,045,811 A | 4/2000 | Dirksing et al. | |
| 6,072,100 A | 6/2000 | Mooney et al. | |
| 6,080,811 A | 6/2000 | Schehlmann et al. | |
| 6,083,421 A | 7/2000 | Huang et al. | |
| 6,086,855 A | 7/2000 | Fischer | |
| 6,096,328 A | 8/2000 | Sagel et al. | |
| 6,106,293 A | 8/2000 | Wiesel | |
| 6,106,812 A | 8/2000 | Prencipe et al. | |
| 6,110,446 A | 8/2000 | Prencipe et al. | |
| 6,121,213 A | 9/2000 | Vergara et al. | |
| 6,136,297 A | 10/2000 | Sagel et al. | |
| 6,149,895 A | 11/2000 | Kutsch | |
| 6,155,832 A | 12/2000 | Wiesel | |
| 6,159,498 A * | 12/2000 | Tapolsky et al. | 424/449 |
| 6,174,516 B1 | 1/2001 | Curtis et al. | |
| 6,190,689 B1 | 2/2001 | Hoffmann et al. | |
| 6,197,331 B1 | 3/2001 | Lerner et al. | |
| 6,221,341 B1 | 4/2001 | Montgomery | |
| 6,241,973 B1 | 6/2001 | Rinne | |
| 6,274,122 B1 | 8/2001 | McLaughlin | |
| 6,277,458 B1 | 8/2001 | Dirksing et al. | |
| 6,280,708 B1 | 8/2001 | Ryles et al. | |
| 6,284,152 B1 | 9/2001 | Kross | |
| 6,290,934 B1 | 9/2001 | Kramer et al. | |
| 6,290,935 B1 | 9/2001 | Masters et al. | |
| 6,306,370 B1 | 10/2001 | Jensen et al. | |
| 6,309,622 B1 | 10/2001 | Watkins | |
| 6,309,625 B1 | 10/2001 | Jensen et al. | |
| 6,312,666 B1 | 11/2001 | Oxman et al. | |
| 6,312,670 B1 | 11/2001 | Montgomery | |
| 6,312,671 B1 | 11/2001 | Jensen et al. | |
| 6,319,510 B1 | 11/2001 | Yates | |
| 6,322,773 B1 | 11/2001 | Montgomery | |
| 6,322,774 B1 | 11/2001 | Jensen et al. | |
| 6,325,997 B1 | 12/2001 | Christopfel | |
| 6,331,291 B1 | 12/2001 | Glace et al. | |
| 6,331,292 B1 | 12/2001 | Montgomery | |
| 6,342,206 B1 | 1/2002 | Gopalkrishnan et al. | |
| 6,348,187 B1 | 2/2002 | Pan et al. | |
| 6,350,437 B1 | 2/2002 | Pasetti et al. | |
| 6,350,438 B1 | 2/2002 | Witt et al. | |
| 6,365,134 B1 | 4/2002 | Orlowski et al. | |
| 6,368,576 B1 | 4/2002 | Jensen et al. | |
| 6,375,933 B1 | 4/2002 | Subramanyam et al. | |
| 6,379,653 B1 | 4/2002 | Aaslyng et al. | |
| 6,391,283 B1 | 5/2002 | Jensen et al. | |
| 6,391,286 B1 | 5/2002 | Mitra et al. | |
| 6,403,060 B1 | 6/2002 | Bornstein et al. | |
| 6,409,992 B1 | 6/2002 | Kleinberg et al. | |
| 6,409,993 B1 | 6/2002 | Jensen et al. | |
| 6,409,994 B1 | 6/2002 | Dahlin | |
| 6,413,502 B1 | 7/2002 | Bornstein et al. | |
| 6,419,902 B1 | 7/2002 | Wright | |
| 6,419,905 B1 | 7/2002 | Alvarez Hernandez | |
| 6,419,906 B1 | 7/2002 | Xu et al. | |

(56) References Cited

U.S. PATENT DOCUMENTS

| | | | |
|---|---|---|---|
| 6,423,300 B1 | 7/2002 | Kleinberg et al. | |
| 6,435,873 B1 | 8/2002 | Burgio | |
| 6,440,396 B1 | 8/2002 | McLaughlin | |
| 6,440,749 B1 | 8/2002 | Cerami et al. | |
| 6,447,757 B1 | 9/2002 | Orlowski et al. | |
| 6,457,469 B1 | 10/2002 | Mueller et al. | |
| 6,458,340 B1 | 10/2002 | Ibsen et al. | |
| 6,458,380 B1 | 10/2002 | Leaderman | |
| 6,471,947 B2 | 10/2002 | Bhakoo et al. | |
| 6,475,472 B2 | 11/2002 | Joiner et al. | |
| 6,479,037 B1 | 11/2002 | Montgomery | |
| 6,485,709 B2 | 11/2002 | Banerjee et al. | |
| 6,488,913 B2 | 12/2002 | Orlowski et al. | |
| 6,488,914 B2 | 12/2002 | Montgomery | |
| 6,500,408 B2 | 12/2002 | Chen | |
| 6,503,485 B1 | 1/2003 | Allred | |
| 6,503,486 B2 | 1/2003 | Xu et al. | |
| 6,509,007 B2 | 1/2003 | Rajaiah et al. | |
| 6,514,483 B2 | 2/2003 | Xu et al. | |
| 6,514,484 B2 | 2/2003 | Rajaiah et al. | |
| 6,517,350 B2 | 2/2003 | Diasti et al. | |
| 6,682,721 B2 | 1/2004 | Kim et al. | |
| 6,689,344 B2 | 2/2004 | Chang et al. | |
| 6,730,316 B2 | 5/2004 | Chen | |
| 6,780,401 B2 | 8/2004 | Kim et al. | |
| 2001/0002252 A1* | 5/2001 | Gallopo et al. | 424/49 |
| 2001/0049417 A1* | 12/2001 | Frate et al. | 525/221 |
| 2002/0081555 A1 | 6/2002 | Weisel | |
| 2002/0141950 A1* | 10/2002 | Chen | 424/53 |
| 2003/0194382 A1 | 10/2003 | Chang et al. | |
| 2005/0031554 A1 | 2/2005 | Kim et al. | |
| 2006/0193793 A1 | 8/2006 | Kim et al. | |
| 2006/0193794 A1 | 8/2006 | Kim et al. | |

* cited by examiner

APPARATUS AND METHOD FOR WHITENING TEETH

CROSS-REFERENCE TO RELATED APPLICATIONS

The present application is a continuation-in-part of U.S. application Ser. No. 10/243,182 filed Sep. 13, 2002, which is a continuation-in-part of application Ser. No. 10/049,817 filed Feb. 19, 2002, which is the national stage of PCT International Application No. PCT/KR01/00207 filed Feb. 13, 2001 designating the United States of America and published in English, and claims the benefit under 35 U.S.C. §119(e) of U.S. Provisional Application No. 60/324,555 filed Sep. 25, 2001, each of which is hereby incorporated by reference in its entirety for all purposes. This application claims the benefit under 35 U.S.C. §119(a) of Korean Patent Application No. 2000-13626 filed Mar. 17, 2000, Korean Patent Application No. 2000-75599 filed Dec. 8, 2000, Korean Patent Application No. 2002 72603 filed Nov. 21, 2002, and Korean Patent Application No. 2003-51912 filed Jul. 28, 2003.

BACKGROUND OF THE INVENTION

The present invention relates to dry type patches for teeth whitening which can be attached to the teeth without using a tray, have a contact area shape capable of minimizing irritation to gums, and have a natural feeling to wearers. Since the patches for teeth whitening strongly adhere to the teeth, they do not disturb the wearer's daily life and are not easily detached from the teeth during the wearer's mouth movements, such as for example, coughing and/or talking in a loud voice.

As people's interest in whitening their teeth increases, a number of tray products providing teeth whitening effects in a short period of time have become commercially available. These tray products are largely divided into over-the-counter products ("OTC products") and products requiring dentist's prescriptions. The OTC products are available in the market at low cost, but are known to have many problems. For example, since the OTC products use one-sized and single-shaped trays, they do not fit various sizes and shapes of users' teeth, which causes irritation to the teeth due to poorly fitting trays and gels excessively applied onto the trays. In addition, since the leakage of gel may take place in use, there are problems in terms of convenience and safety. Further, since most of the OTC products are highly noticeable, it is difficult to use them in daily life. Accordingly, the OTC products are limited in their use, for example, for overnight use only. On the other hand, since the products requiring dentist's prescriptions are precisely manufactured according to the contour and size of patient's teeth, the problems of the OTC products can be solved to some extent but are disadvantageous in that they are expensive and a patient needs to regularly see a dentist.

To overcome the above problems of the gel-filled tray products, strips for teeth whitening without the use of trays have been developed and a number of patent applications related thereto have been filed. For instance, U.S. Pat. No. 5,310,563 ("Curtis et al.") suggested a strip for teeth whitening which comprises a capsule obtained by encapsulating a peroxide or various ingredients in a putty-like material using a silicon polymer. The adhesion of the strip for teeth whitening to the teeth results from the elasticity of the putty such as rubber. However, meaningful attention is not given to the shape of the strip. The strip has a drawback that since the peroxide is encapsulated in the putty-like material, the whitening effects are relatively poor although the strip is attached to the teeth for the same time period. Further, since the adhesion between the strip and the teeth depends on the elastic strength, some stimuli to the teeth, such as coughing or collision with something, in a mouth in which a tongue actively moves may separate the strip from the teeth and thus the strip is returned to its initial shape.

On the other hand, 3M developed a strip for teeth whitening using only a gel retention insert without the use of a tray. The gel retention insert is a product that was developed in order to further enhance the adhesion between gel and the teeth, and has a microstructure. The gel retention insert used as the strip for teeth whitening has a microstructure in which a PSA (pressure sensitive adhesive) is used and teeth whitening ingredients are dispersed. However, the teeth whitening effects of the gel retention insert are not verified, like trays manufactured using a gel retention insert having a water-insoluble microstructure. Since most polymers used as PSAs employ solvents unsuitable for oral products, e.g., methylene chloride or ethylacetate, etc, instead of water or alcohol, they are considered to be unsuitable to directly attach to the teeth in the oral cavity. In addition, in the case that an acrylic polymer (a wet PSA) having a low compatibility with a peroxide is used as a strip for teeth whitening, the strip for teeth whitening is thought to be inappropriate for commercialization.

U.S. Pat. No. 6,419,906, issued to Colgate, discloses a strip for teeth whitening comprising a thermoplastic ethyleneoxide polymer and a solid percarbonate as a teeth whitening agent. However, since the ethyleneoxide polymer is highly compatible with the peroxide but has a low adhesion to the teeth, it is believed that the wearability of the strip is poor.

In particular, such strips for teeth whitening were commercialized by P&G. Since the strip for teeth whitening is manufactured by uniformly and thinly applying teeth whitening ingredients onto a thin and flexible polyethylene strip without the use of a tray, problems of conventional tray products can be solved. Since the strip for teeth whitening is a wet type, the adhesive strength of the strip to the teeth is not so strong. Accordingly, the strip can be easily attached and peeled off, but has a drawback in that when coughing and laughing out loud, it is not attached at a desired position for a desired period of time and can be easily detached from teeth, in particular, from lower teeth in comparison to upper teeth. As a patented product associated with these strip products, a strip with rounded corners is disclosed in U.S. Pat. No. 5,879,691. Thereafter, based on the finding that a particular shape a strip for teeth whitening is essential to attach a teeth whitening agent to a desired site for a desired time, P&G developed a strip having various shape and filed PCT publication WO 2001-014736. The strip for teeth whitening has a shape in which the outer surface of 4 front teeth and 2 canine teeth is covered while allowing the tips of the two canine teeth to be uncovered. That is, the strip is of a shape that the tips of the canine teeth are uncovered. Possible examples of the strip shape include trapezoids with or without at least one stepped side or notch and quadrangles with at least one stepped side, notch or recess. These shapes allow the strip and teeth whitening materials to adhere well to the teeth, and maintain the state without sliding from the wearer's teeth for a long period of time. As can be seen from commercialized strip products for teeth whitening manufactured by P&G, the strip products are applied to lower teeth having a relatively large size and less curved rather than upper teeth. FIGS. 1a and 1b are plan views of a strip for upper teeth and a strip for lower teeth of Crest Whitestrip (P&G), respectively.

However, although the strip for teeth whitening manufactured by P&G has a trapezoidal shape such that the tips of 2 canine teeth are not covered with the strip, the adhesion of the strip to the teeth is poor because the strip is a wet type. Accordingly, there is a need to improve the problem of poor adhesion.

The primary benefit of a dry type patch for teeth whitening, which was filed by the present inventors, is that when a user peels off the patch from a release liner using the hands and attaches the patch to the teeth, adhesive ingredients contained in an adhesive layer are not deposited on the hands and unwanted sites, e.g., the face and lips, due to user's error. In addition, since the patch is a dry type, it solves safety problems caused by a high concentration hydroxide used as a teeth whitening agent. That is, after the dry type patch is attached to the teeth, a glassy polymer provides strong adhesion to the teeth while being hydrated by moisture on the tooth surface and a whitening agent begins to be released. Accordingly, the dry type patch is a safe formulation having no problem in use.

However, despite these advantages of the dry type patch for teeth whitening discussed above and excellent adhesion to the teeth, when the patch comes into contact with gums containing a higher level of moisture than the teeth, the strong adhesive strength induced during hydration may cause irritation to gums.

SUMMARY OF THE INVENTION

Therefore, the present invention has been made in view of the above problems of patches for teeth whitening (e.g., irritation to gums by moisture contained therein), and it is an object of the present invention to provide dry type teeth whitening patches for upper and lower teeth wherein the shape of the patch and/or the contact area is formed along the gum line between the teeth and gums in order to minimize the contact with gums.

In order to accomplish the object of the present invention, there is provided a pair of dry type patches for teeth whitening having a patch for upper teeth and a patch for lower teeth, in which the patch for upper teeth has a shape different from the patch for lower teeth, and each patch and/or contact area has a controlled width and shape such that the contact area of each patch with gums is minimized. It is preferred that a central portion covering right and left upper central incisors is widest in the patch for upper teeth, and either portion covering right and left lower canine teeth is widest in the patch for lower teeth.

In accordance with one aspect of the present invention, there is provided dry type patches in which a hydrophilic glassy polymer is used for various layers including an active ingredient-containing layer. Since the dry type patches of the present invention can provide sufficient contact of teeth whitening agent with stains formed on tooth surface, excellent whitening effects can be obtained in a short period of time.

Embodiments of the present invention overcomes the problems of the conventional dry type patches (e.g. strong irritation to gums upon attaching to the teeth in oral cavity). Thus, embodiments of the present invention relates to a shape in which the contact area with gums is minimized upon attaching the patch to the teeth for reducing irritation to gums, and area folded into the back portion of the teeth is minimized by using strong adhesion to the teeth, which is an advantage of the dry type patch. Therefore, some embodiments of the present invention provide dry type patches for teeth whitening comprising peroxide, which are well fitted with the contour of teeth and minimizing the contact with gums.

Embodiments of the present invention relates to dry type patches for teeth whitening which exhibit excellent adhesion to teeth and have a shape capable of reducing irritation to gums. Dry type patches, a preferred embodiment of the present invention, maintain the inherent advantages, and at the same time, solve the disadvantages of conventional dry type patches. In addition, the shape of the contact area of the patch according to the present invention is formed along the contact line (e.g. gum line) between the teeth and gums in order to whiten the roots of teeth while minimizing the contact of the contact area with gums. Accordingly, it is preferred that a central portion covering right and left upper central incisors is widest (convex) in the patch for upper teeth because upper central incisors are largest and highest among upper teeth, and either portion covering right and left lower canine teeth is widest and the other portion is concave in the patch for lower teeth because the canine teeth are exposed in the largest portion among lower teeth.

People want white teeth since white teeth increase self-confidence during conversation and leave a bright image in other people's minds. The number of teeth exposed when smiling or talking is commonly 4~8 in both the upper and lower teeth. Some people want to whiten unseen back surface as well as visible front surface of all teeth. In the most of people, however, the color of front teeth is of primary importance. It is known that the canine teeth are the more popular to be colored, compared to the rest of front teeth. In addition, the roots of teeth (close to gums) are the more popular to be colored than the tips of teeth (distant from gums). It is also known that when a teeth whitening product containing peroxide is used to whiten teeth, upper teeth and tooth tips (distant from gums) are rapidly whitened in comparison to the lower teeth and roots of the teeth. The shape of the dry type patches, or at least the contact area of the dry type patch, preferably contains peroxide and is formed along a line covering the roots of teeth while minimizing the contact area with gums.

Since peroxides commonly used as a teeth whitening agent bleaches not only stains formed on tooth surface, but also enamel and dentin of teeth, they are known to have excellent whitening effects. However, there is a possibility of the peroxides permeating into gums. Although peroxides are proved to be safe in toxicity tests, peroxides may transiently cause irritation upon being touched to gums. As the transient irritation caused by peroxides, tooth sensitivity and gingival irritation are generally known. It is known that the irritation may be severe when a product containing peroxide is used immediately after brushing the teeth. It is also known that the irritations may be frequently caused when a peroxide product is continuously used. In order to reduce the transient irritation, the use of the peroxide product in areas that come in contact with the gums should be stopped or minimized. It is preferable that little or no irritation is caused by the peroxide product. It is generally known that any product containing peroxide of low concentration and low content is effective in reducing the irritations. However, since the whitening effects of teeth whitening products are proportional to the concentration and content of peroxide, it is preferred to appropriately control the level of peroxide.

Preferred shapes of a patch for teeth whitening may vary depending on the components and characteristics of the embodiment of the patch and/or the embodiment of the contact area of the patch. For instance, since Crest Whitestrips (P&G), which is a typical wet type strip for teeth whitening, has weak adhesive strength, it can be readily attached to and peeled off from teeth at a desired time. In addition, since the adhesive strength of the strip results from Carbopol gel, an adhesive polymer, contained in the strip, there is no difference between the adhesion of the strip's contact area to teeth and to gums. However, since the adhesive strength of the strip is weak, the strip may be detached from teeth by various stimuli. Accordingly, it is preferred that the strip has a shape to be folded into the back portion of teeth without covering the tip of canine teeth. That is, the strip preferably covers both front and back portion of teeth in such a way not to be detached from teeth.

On the other hand, as a general dry type patch is hydrated, it has strong adhesive strength. Accordingly, gums containing higher level of moisture than teeth are first hydrated and strongly adhere to the patch. Further, while being maintained in the condition attached to teeth, peroxide contained in the patch permeates into gums to cause more irritation. For such reasons, it is preferred that the contact area between the patch and gums is minimized. As described above, since the roots of teeth close to gums are severely colored but slowly whitened compared to teeth tips, the roots of teeth are preferably covered with the patch. The patch may have a folded line to cover the back portion of the teeth. However, since lower teeth are frequently touched by tongue, a small folded portion is preferred in terms of wearability. Preferably, the contact area of the patch for lower teeth has a width of 0.3~2 cm, preferably 0.5~1.5 cm so as to completely cover the front portion but partially or not at all cover the back portion of lower teeth. In case that the patch for lower teeth has a contact area width of 2~4 cm, the front and back portions of lower teeth are completely covered. Like the patch for lower teeth, a small folded portion of the patch for upper teeth is preferred in terms of wearability. Preferably, the patch contact area for upper teeth has a width of 0.5~2.5 cm, preferably 0.7~1.5 cm so as to completely cover the front portion but partially or not at all cover the back portion of upper teeth.

The size of the patches and or patch contact areas for teeth whitening may vary depending on the number and size of teeth. The patches of the present invention can be applied, regardless of the number and position of teeth. When the patches are attached to only one tooth, the color of the tooth may be different from the other teeth, which is not preferable. When the patch is applied to all teeth, a user must open his mouth as widely as possible to attach the patches to teeth, which is very inconvenient. Accordingly, it is preferred that the patches have a size sufficient to cover 6 to 8 teeth exposed when smiling and talking.

The patches for teeth whitening may have a rectangular shape which has the same width. However, when the width is adjusted to the largest tooth, the patches completely cover the other small teeth and touch the gum portion. Alternatively, when the width is adjusted to the medium-sized tooth, the patches cannot completely cover the roots of the relatively large teeth.

Since upper teeth are different from lower teeth in terms of their size, contour and curvature, the patch for upper teeth has preferably a shape different from the patch for lower teeth. For example, the patch for upper teeth is preferably manufactured in such a manner that a central portion covering right and left upper central incisors is widest (convex) because upper central incisors are largest and highest among upper teeth, and the patch for lower teeth is preferably manufactured in such a manner that either portion covering right and left lower canine teeth is widest because the canine teeth are exposed to the largest extent among lower teeth. Many people have upper teeth having a size of about 1 cm and lower teeth having a size of about 0.9 cm on average. Thus, the contact areas of the patches of the present invention preferably has a width of 0.8~1.5 cm for upper teeth and a width of 0.6~1.5 cm for lower teeth.

In view of the foregoing, since the dry type patches of the present invention have excellent adhesiveness to the wearer's teeth, it cannot be detached from teeth without an externally applied force. Accordingly, the present invention provides dry type teeth-whitening patches for both the upper and lower teeth wherein the patch contact area shape is formed along the contact line between the teeth and gums in order to minimize irritation to gums and obtain excellent whitening effects.

A major advantage of the dry type patches for teeth whitening according to the present invention is that since the patches have strong adhesive strength after their hydration, it can be fixed to the teeth for a sufficient period of time without any folded portion at the back portion of the teeth. In addition, the dry type patches have advantages of providing natural feeling to wearers and have a minimized contact area between the patch and gums, thereby causing no or little irritation to gums. Furthermore, the patch for upper teeth does not contact with the patch for lower teeth, which provides good wearability. However, since the patch for lower teeth may be diluted by saliva, it may be detached from lower teeth after the attachment in a short time. In case of folded type of patches, in which the patch for lower teeth is folded toward the back portion so that it surrounds the lower teeth, the dilution by saliva is decreased and the patch for lower teeth can be attached to the lower teeth for a desired period of time.

In order to maximize the whitening effect of the dry type patches for teeth whitening, it is preferred to lengthen the contact time between the whitening agent and stains on teeth, preferably for overnight. The first dentist-prescribed at-home bleaching product using a fixed tray was intended for overnight-use. Since wet type patch products have a weak adhesion to teeth, they are unsuitable for overnight-use. Whereas, since dry type patch products have a strong adhesion to teeth, they are suitable for overnight-use. Dry type patch products having a folded portion are more preferred in terms of improved adhesive strength.

Since teeth whitening effect is enhanced particularly in a sealed environment, it is expected that the folded dry type patch can exhibit excellent teeth whitening effect.

In order to increase adhesive strength to teeth and minimize unnatural feeling of wearers, cut lines are formed in the folded dry type patches. More preferably, broad cut lines are formed to minimize the overlapped portions at the back of lower teeth. The wearer feels unnatural and unpleasant because the folded area at the back of teeth is relatively narrow at canine teeth or before, while the folded area at the back of teeth is relatively wide next to the canine teeth. Accordingly, the patch for lower teeth is preferable to cover only the back of teeth at canine teeth or before.

In addition, it is preferred to make a notch at the central portion of the patches for upper teeth and lower teeth. The formation of notch is advantageous in term of wearability. When wearing the dry type patches, the notch allows the patches to be fitted to the central line of teeth. Particularly, when the notch is formed at the center of the central portion of the patch for upper teeth, the contact area of the patch with gums is minimized and thus irritation to gums is reduced.

BRIEF DESCRIPTION OF THE DRAWINGS

The accompanying drawings, which are incorporated in and form a part of the specification, illustrate sample embodiments of the present invention and, together with the description serve to explain the principles of the invention. Additional embodiments are within the scope of the invention. In the drawings:

FIG. 1a is a plan view showing a Crest Whitestrip (P&G) for lower teeth;

DETAILED DESCRIPTION OF THE PREFERRED EMBODIMENTS

Figure 2A:
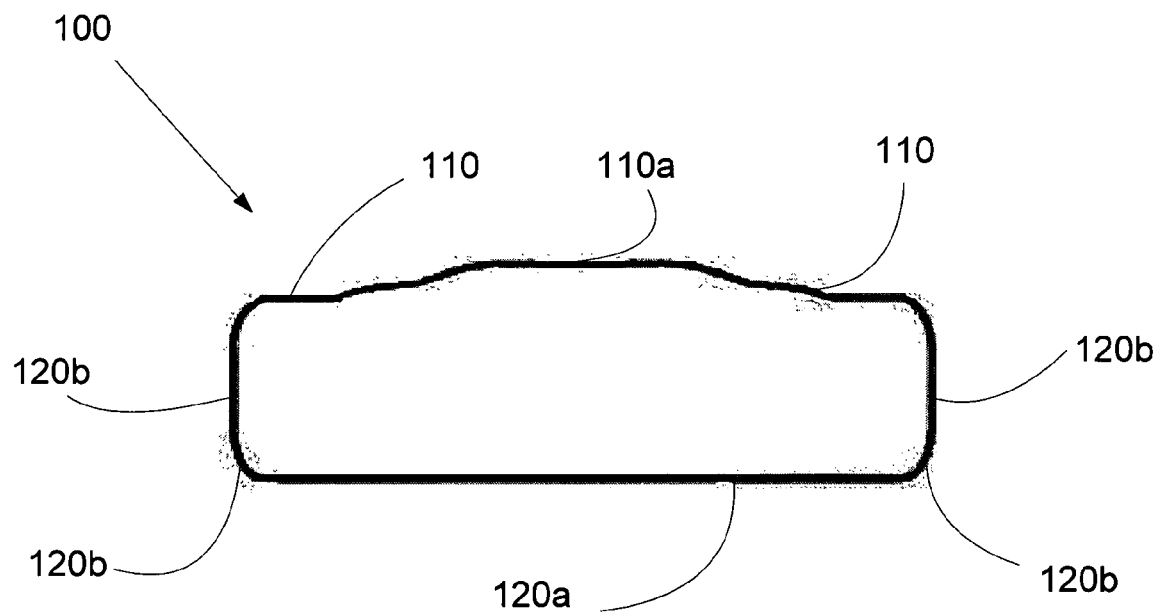
FIG. 2a is a plan view showing a contact area of a teeth-whitening patch for upper teeth in accordance with a first one of the preferred embodiments of the present invention.
Figure 2B:
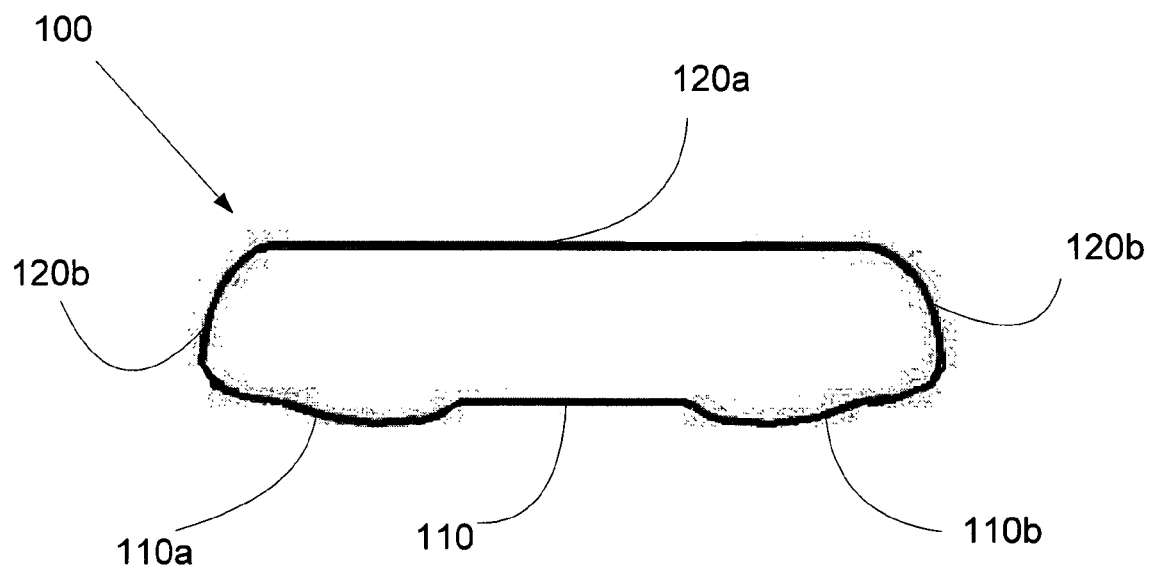
FIG. 2b is a plan view showing a contact area of a teeth-whitening patch for lower teeth in accordance with a second one of the preferred embodiments of the present invention.

Referring to FIGS. 2a and 2b, embodiments are shown of a contact area of a teeth-whitening patch that are designated generally 100. Each contact area 100 shows a gum line perimeter segment 110 and at least one other perimeter segment 120. The shown embodiment of at least one other perimeter segment 120 comprises an opposing perimeter segment 120a and a plurality of side perimeter segments 120b. Gum line perimeter segment 110 and at least one other perimeter segment 120 are joined to define the shape of contact area 100. As shown, the at least one other perimeter segment can be either linear or curved.

FIG. 2a shows a plan view of a contact area for upper teeth in which the gum line perimeter segment comprises a wide portion 110a, centrally located, that covers the most protruded upper central incisors, which are the widest upper teeth. FIG. 2b shows a plan view of a contact areas for lower teeth in which two wide portions 110b cover the right and left lower canine teeth, which are the widest lower teeth.

Figure 3A:
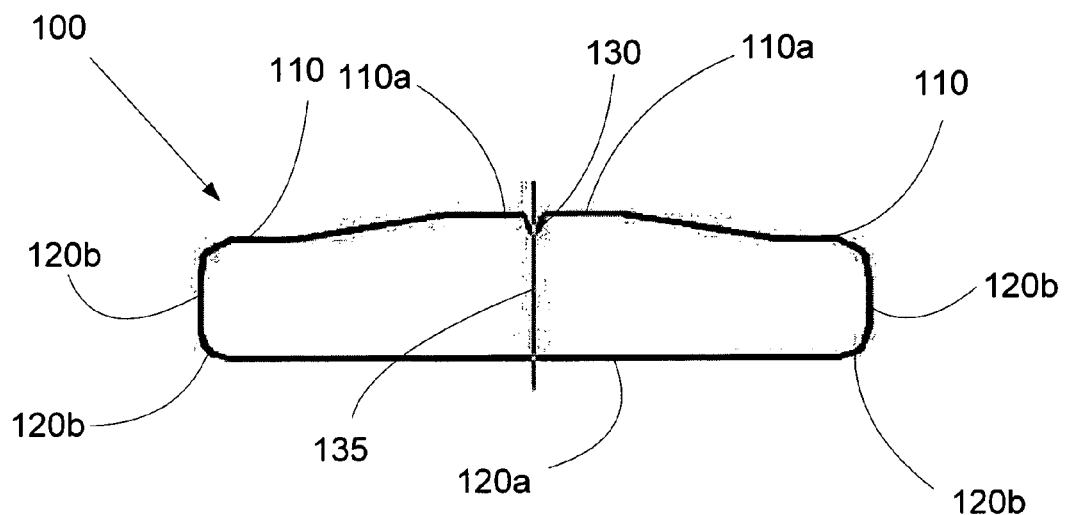
FIG. 3a is a plan view showing a contact area of a teeth-whitening patch for upper teeth in accordance with a third one of the preferred embodiments of the present invention.
Figure 3B:
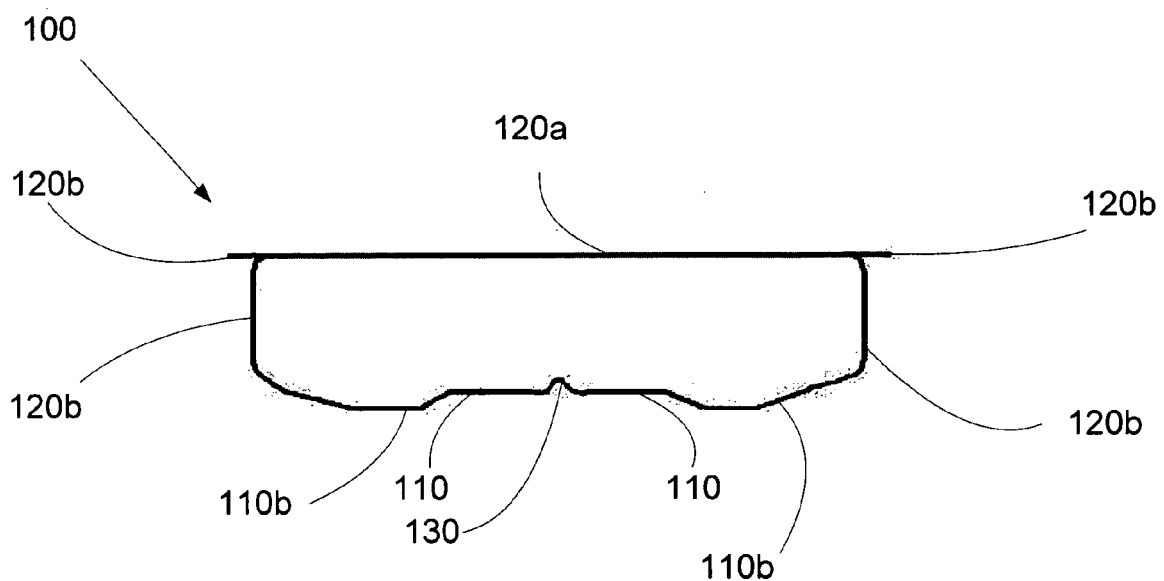
FIG. 3b is a plan view showing a contact area of a teeth-whitening patch for lower teeth in accordance with a fourth one of the preferred embodiments of the present invention.

Referring to FIGS. 3a and 3b, additional embodiments of a contact area 100 are shown. FIG. 3a shows a plan view of a contact area for upper teeth in which the gum line perimeter segment comprise wide portion 110a, centrally located, that covers the most protruded upper central incisors, which are the widest upper teeth. A physical notch 130 is formed at the center of wide portion 110a (the center of gum line perimeter segment 110) so contact area 100 can be conveniently attached to the upper teeth by aligning notch 130 with the center of the upper teeth. As and addition or alternative to notch 130, other alignment indicia may be utilized, such as for example, graphical indicia such as line 135.

FIG. 3b shows a plan view of a contact area for lower teeth in which two wide portions 110b cover the right and left lower canine teeth, which are the widest lower teeth. A physical notch 130 is formed at the center of gum line perimeter segment 110 so contact area 100 can be conveniently attached to the lower teeth by aligning notch 130 with the center of the upper teeth. In addition to or as an alternative to notch 130, other alignment indicia may be utilized, such as for example, graphical indicia such as line 135.

Figure 4A:
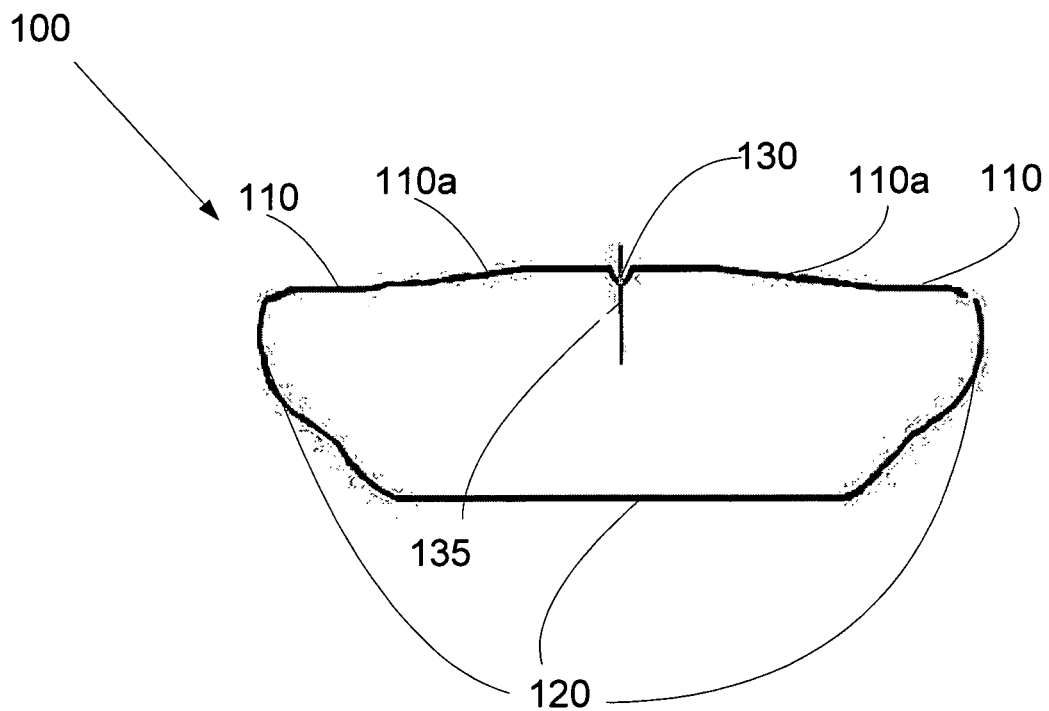
FIG. 4a is a plan view showing a contact area of a teeth-whitening patch for upper teeth in accordance a fifth one of the preferred embodiments of the present invention.
Figure 4B:
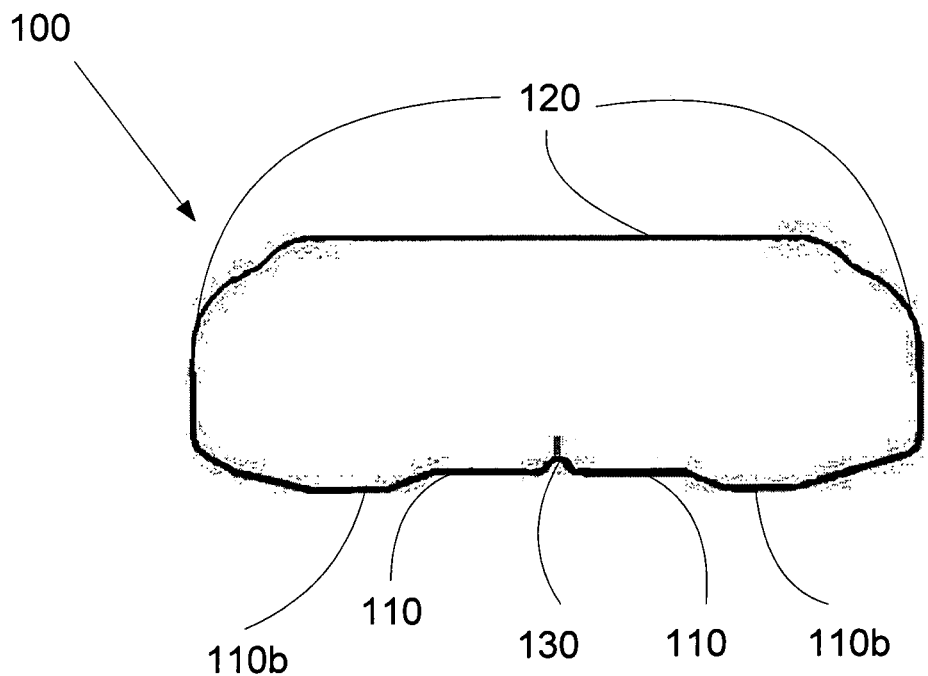
FIG. 4b is a plan view showing a contact area of a teeth-whitening patch for lower teeth in accordance with a sixth one of the preferred embodiments of the present invention.

Referring to FIGS. 4a and 4b, additional embodiments of contact area 100 are shown. FIG. 4a shows a plan view of contact area 100 for upper teeth in which central portion 110a covering the most protruded upper central incisors among upper teeth is widest. Notch 130 is formed at the center of central portion 110a (at the center of gum line perimeter portion 110) so contact area 100 can be conveniently attached to the upper teeth by aligning notch 130 with the center of the upper teeth. Contact area 100 is further defined by at least one other perimeter segment 120 that extends to as to cover the back portion of the upper teeth when contact area is folded over the tips of the teeth. In preferred embodiments, the chosen dimensions of contact area 100 are sized so that contact area does not hit the gums behind the upper teeth when contact area 100 is folded over the tips of the teeth.

FIG. 4b shows a plan view of contact area 100 for lower teeth in which two wide portions 110b cover the right and left lower canine teeth. Notch 130 is formed at the center of gum line perimeter portion 110 so contact area 100 can be conveniently attached to the upper teeth by aligning notch 130 with the center of the lower teeth. Contact area 100 is further defined by at least one other perimeter segment 120 that extends to as to cover the back portion of the upper teeth when contact area is folded over the tips of the teeth. In preferred embodiments, the chosen dimensions of contact area 100 are sized so that contact area does not hit the gums behind the lower teeth when contact area 100 is folded over the tips of the teeth.

Figure 5A:
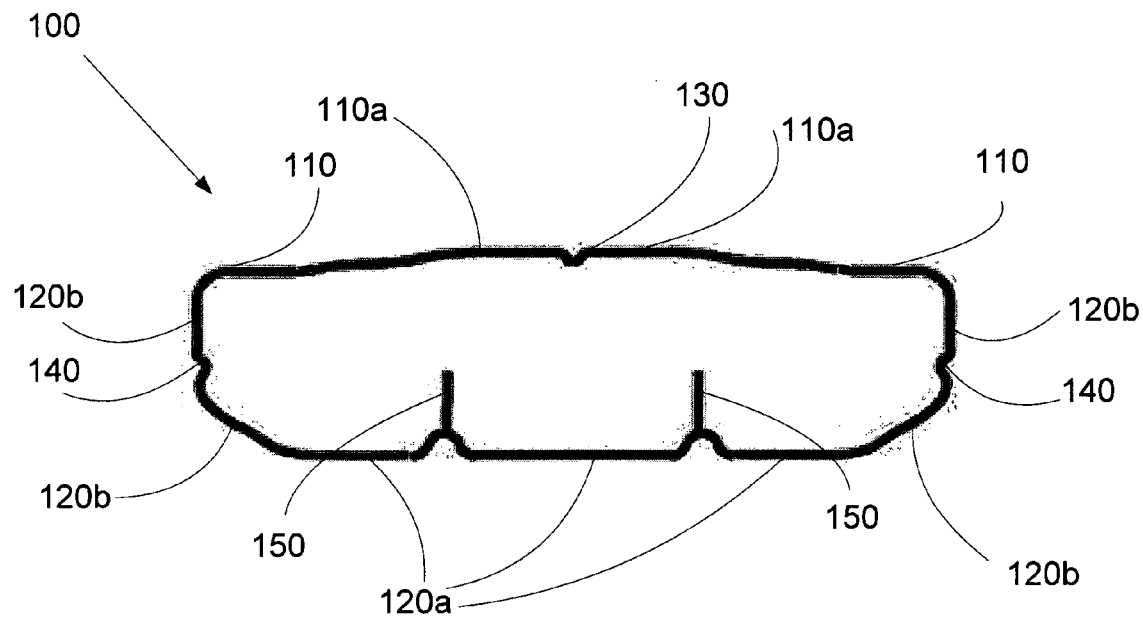
FIG. 5a is a plan view showing a contact area of a teeth-whitening patch for upper teeth in accordance with a seventh one of the preferred embodiments of the present invention.
Figure 5B:
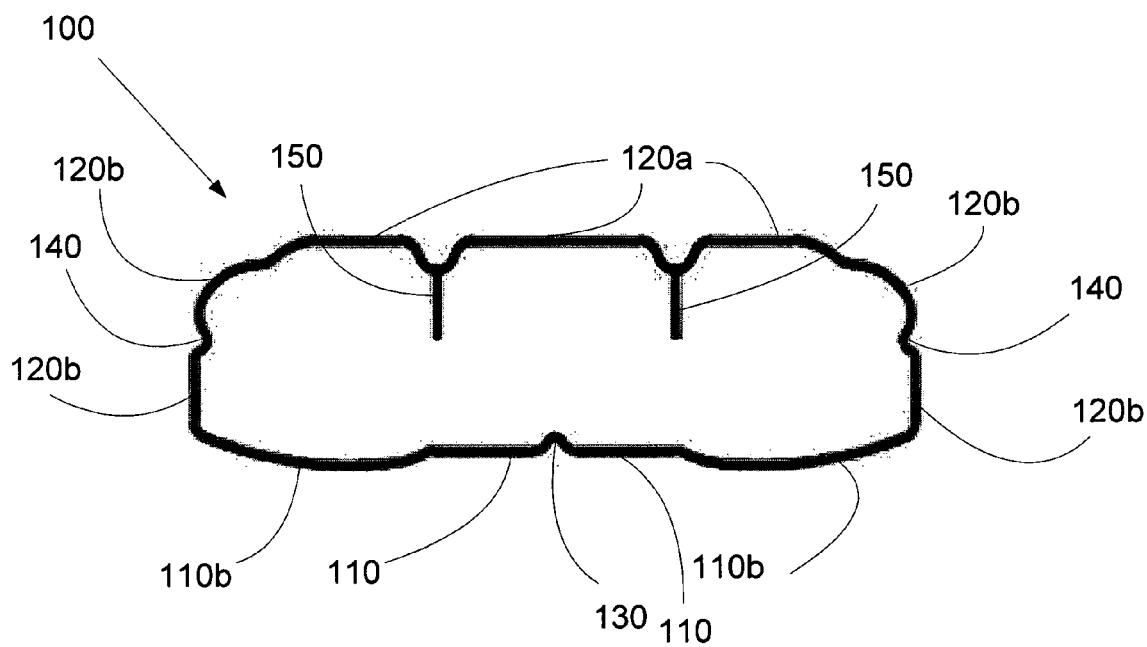
FIG. 5b is a plan view showing a contact area of a teeth-whitening patch for lower teeth in accordance with an eighth one of the preferred embodiments of the present invention.

Referring to FIGS. 5a and 5b, additional embodiments of contact area 100 are shown. FIG. 5a shows contact area 100 with side notches 140 on side perimeter segments 120b for alignment of a folding axis with the tip of the upper teeth. Contact area 100 includes at least one cut line 150 that preferably runs from opposing perimeter segment 120a through contact area 100 in a direction substantially perpendicular to the point of opposing perimeter segment 120b where opposing perimeter segment 120b intersects with at least one cut line 140. FIG. 5b shows contact area 100 with side notches 140 on side perimeter segments 120b for alignment of a folding axis with the tip of the lower teeth. Contact area 100 includes at least one cut line 150 that preferably runs from opposing perimeter segment 120a through contact area 100 in a direction substantially perpendicular to the point of opposing perimeter segment 120b, where opposing perimeter segment 120b intersects with at least one cut line 150.

Not all individuals have exactly the same teeth dimensions. The at least one cut line 150 facilitates customization of contact area 100 to individuals having varying teeth dimensions and facilitates easy folding to the back portion of the teeth. When contact area 100 is folded over the tips of the upper teeth, at least one cut line 150 allows portions of contact area to fold over the tips of upper teeth at different angles. This play facilitates high quality folding, where the tooth coverage of contact area 100 is substantially maximized.

Figure 6A:
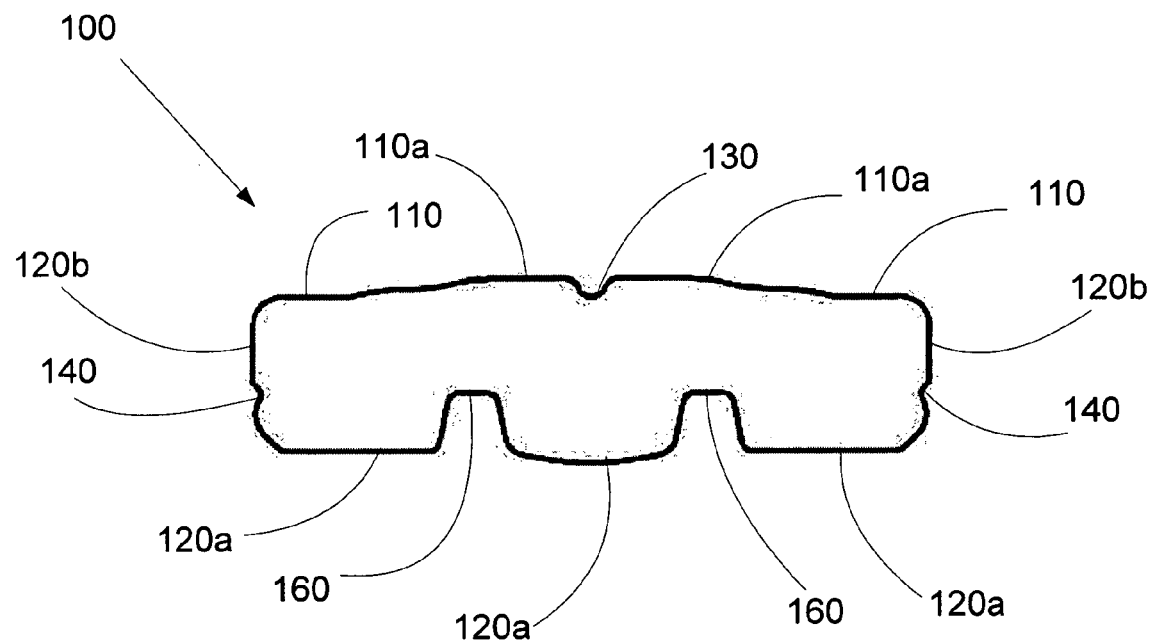
FIG. 6a is a plan view showing a contact area of a teeth-whitening patch for upper teeth in accordance with a ninth one of the preferred embodiments of the present invention.
Figure 6B:
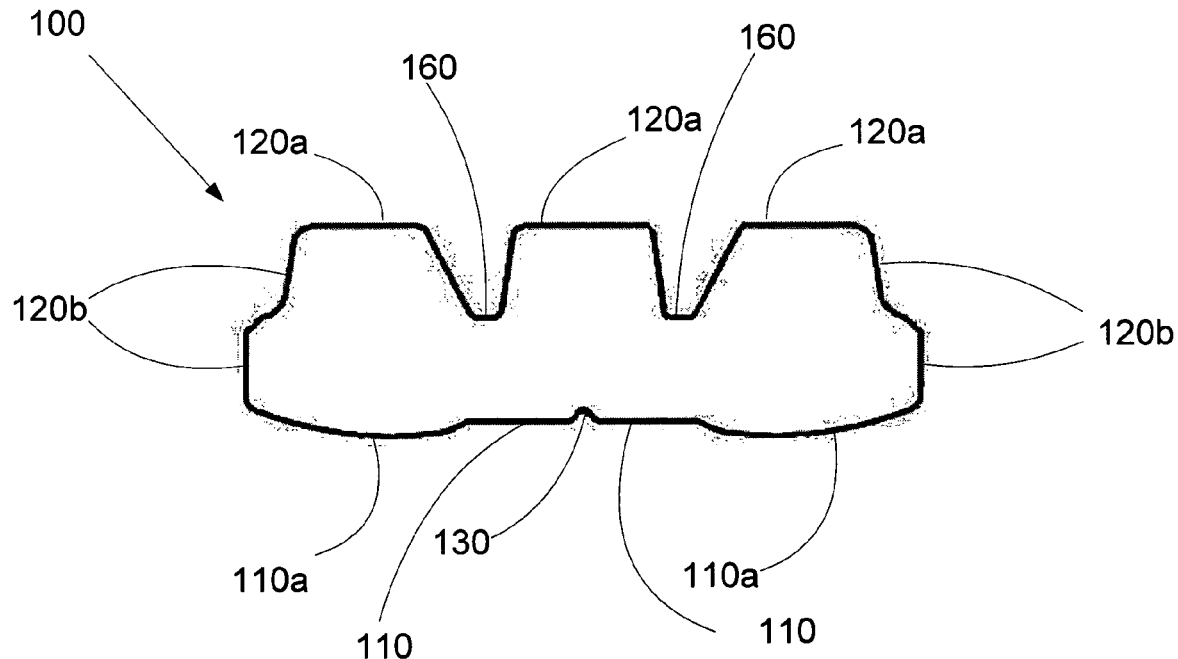
FIG. 6b is a plan view showing a contact area of a teeth-whitening patch for lower teeth in accordance with a tenth one of the preferred embodiments of the present invention.

Referring to FIGS. 6a and 6b, additional embodiments of contact area 100 are shown. FIG. 6a shows contact area 100 with side notches 140 on side perimeter segments 120b for alignment of a folding axis with the tip of the upper teeth.

Opposing perimeter segment 120b also includes recessed perimeter segments 160 that are positioned on contact area 100 so that recessed perimeter segments 160 align with upper lateral incisors when the contact area 100 is aligned on the front surface of the upper teeth. FIG. 6b shows an analogous contact area 100 for the lower teeth. Opposing perimeter segment 120b also includes recessed perimeter segments 160 that are positioned on contact area 100 so that recessed perimeter segments 160 align with the lower lateral incisors when the contact area 100 is aligned on the front surface of the lower teeth. In this respect, the tooth contact surface does not contact the tips of the lateral incisors when properly aligned against a tooth surface.

It should be understood that the patches and/or contact areas for teeth whitening of the present invention is not limited to the shapes shown in the above figures. Considering the contour of upper teeth, central portion 110a is most likely to contact with gums. For this reason, notch 130 formed at central portion 110a is preferably two times longer than notch 130 formed at the central portion 110 for lower teeth to reduce the contact area of contact area 100 with gums, which allows more convenient use. Lower teeth are highly curved, compared to upper teeth. When cut lines 150 are too narrowly formed at the folded portion of the contact area 100 for lower teeth, overlapped portions occur at the back portion of the lower teeth, which causes an unnatural feeling and inconvenience in use. Accordingly, it is preferred to form two or more broad cut lines 150 at the folded portion of the patch for lower teeth.

In order to manufacture the dry type patches for teeth whitening of the present invention, a hydrophilic glassy polymer is used to form layers including an adhesive layer, active material-containing layer and the other layers just except a backing layer. The hydrophilic glassy polymer provides strong adhesion to teeth and releases a teeth whitening agent while being hydrated at the enamel layer of teeth in moist oral cavity.

A patch for teeth whitening using no tray (e.g. non-tray type) exhibits excellent teeth whitening effect only by attaching the patch to teeth. However, when the patch includes a wet adhesive layer, and particularly is gel-type, it may leave a considerable amount (80% or more) of active material or adhesive material on hands upon peeling off the patch from a release liner. Further, when the patch is contacted with user's face or lips due to the user's mistake, adhesive material contained in the adhesive layer remains in the face or lips. Moreover, undesired results may be obtained depending on the kind or content of the teeth whitening agent. Particularly, since a high concentration peroxide having an excellent bleaching effect is used as a teeth whitening agent, serious problems may occur. On the contrary, active material and adhesive material contained in the dry type patch of the present invention are maintained in the state of a solid (sheet or film) before hydration. When the patch is touched to skin or detached from teeth, the active material and adhesive material are left in a small amount of 0~10%. Accordingly, the dry type patches of the present invention are proved to be safe and convenient to use.

Non-tray patches or trays for teeth whitening are required to show excellent adhesive strength comparable to physical properties of mucoadhesives, e.g., AFTACH (Distributor: Dong-Wha Pharm. Ind. Co., Ltd., Korea, Manufacturer: TEIJIN, Japan) and Taisho-A (Distributor: Taisho Pharmaceutical Co., Ltd., Japan, Manufacturer: TEIYAKU, Japan), used for treating stomatitis. That is, they must have adhesive strength sufficient to exhibit desired effect in moist oral cavity for a desired period of time. In addition, they are required to have adhesive strength so as not to be detached from teeth even in unexpected situations, e.g., sudden coughing and shouting in a loud voice. Furthermore, it is preferred that the non-tray patches or trays for teeth whitening have low adhesive strength prior to attachment to the teeth. This is because too strong an initial adhesive strength may cause problems upon detaching from a release liner using hands.

The dry type patches of the present invention may easily solve such problems. The dry type patches of the present invention have very low adhesive strength before the patches are hydrated. The dry type patches provide strong adhesive strength after hydration. Even when the dry type patches are completely hydrated, it can be easily detached using hands. If the adhesion to the teeth is too strong, drinking of a large amount of water (mouthwash, brushing, drinking water or beverage) facilitates the detachment from teeth. Accordingly, the dry type patches of the present invention are advantageous in terms of convenience in use.

The backing layer may contain a water-insoluble and water-impermeable polymer as a film formed in order to prevent the patch from sticking to gums or tongue and from deforming or being detached from teeth by saliva.

On the other hand, there may be a problem that peroxide used as a teeth whitening agent in dry type patches for teeth whitening becomes unstable as time goes by. In order to solve the instability of peroxide in the present invention, a peroxide stabilizer may be used, or a solution of a glassy polymer having a good compatibility with peroxide is added by adjusting the solvent ratio without using peroxide stabilizer. Thus, the present invention provides a new type patch in which a hydrophilic glassy polymer is used as a base polymer for an adhesive layer of a dry type patch using a peroxide as a teeth whitening agent, and a peroxide stabilizer or a solution of a glassy polymer having a good compatibility with the peroxide is added by adjusting the solvent ratio, instead of the peroxide stabilizer. The new type patch of the present invention can ensure the stability of peroxide.

In order to enhance the whitening effect of the patches for teeth whitening according to the present invention, a polyphosphate may be used together with peroxide as a teeth whitening agent.

The teeth whitening effect of the patches for teeth whitening according to the present invention may be controlled by adjusting the thickness of the patches or by varying active material. As soon as the patch is worn, it begins to be hydrated and becomes transparent. In addition, since the backing layer has no pattern or pocket thereon, it is possible for wearers to observe oxygen bubbles generated by peroxide upon wearing, and thereby to visibly recognize the whitening effects. Also, since the patch is transparent and not conspicuous upon wearing, the user's daily life is not affected.

The patches for teeth whitening of the present invention are matrix type patches, and are intended to be attached not to skin or mucous membrane but to the enamel layer of teeth so as to supply a teeth whitening agent to the surface of teeth for a sufficient time to whiten the teeth. The principle that the patches are attached to teeth and the teeth whitening agent contained in the matrix is released onto the surface of teeth is described below: In the field of transdermal drug delivery systems with time lag, there has been suggested a transdermal formulation using moisture transpired from skin to release a drug when a predetermined time passes after its attachment. More particularly, a barrier impermeable to the drug is provided between a drug reservoir and a skin adhesion surface in the transdermal formulation. When the formulation is attached to skin, the barrier is gradually hydrated by moisture transpired from skin, whereby its permeability to the drug is increased. In this case, a hydrophilic glassy polymer is used as the barrier material. In the present invention, a hydrophilic glassy polymer is used as a material for various layers of the matrix type patch. By this patch structure, the release of a whitening agent is prevented when storing and attaching the patch to teeth using hands. After the patch is attached, the patch begins to be hydrated by moisture on the tooth surface and thus adhesive strength is obtained so that the whitening agent is released. A hydrophilic glassy polymer is used as a material for various layers of the matrix type patch. Therefore, in accordance with another aspect of the present invention, a hydrophilic glassy polymer is used as a material for layers of the matrix type patch other than the backing layer.

For these purposes, examples of the glassy polymer which can be used in the adhesive layer of the patch according to the present invention include polyalkylvinyl ether-maleic acid copolymer (PVM/MA copolymer) such as Gantrez AN 119, AN 139 and S-97, polyvinyl alcohol, polyacrylic acid, Poloxamer 407 (Pluronic), polyvinyl pyrrolidone-vinyl acetate copolymer (PVP/VA copolymer) such as Luviskol VA and Plasdone S PVP/VA, polyvinyl pyrrolidone (PVP, K-15~K-120), Polyquaternium-11 (Gafquat 755N), Polyquaternium-39 (Merquat plus 3330), Carbomer (Carbopol), hydroxypropylmethyl cellulose, hydroxyethyl cellulose, hydroxypropyl cellulose, gelatin and alginate salt such as sodium alginate. The above-described polymers can be used alone or in mixtures thereof. Solvents for these polymers include water, ethanol or mixtures thereof with varied mixing ratios.

The patch to be attached onto teeth should be flexible enough to be deformable so that it conforms to contours of teeth. Since some polymers have poor flexibility, suitable plasticizers may be added. The plasticizer is dependent on the kind and preparation of the glassy polymer, but polypropylene glycol, glycerin or polyethylene glycol is generally used as the plasticizer.

The teeth whitening agent contained in the tooth enamel adhesive layer may be selected from the group consisting of hydrogen peroxide, carbamide peroxide, calcium peroxide, sodium percarbonate, sodium perborate, tetrasodium pyrophosphate peroxidate and mixtures thereof. Tetrasodium pyrophosphate peroxidate ($TSPP-H_2O_2$), which is an addition compound of tetrasodium pyrophosphate and hydrogen peroxide, displays properties of tetrasodium pyrophosphate, per se, as well as properties of hydrogen peroxide in a state of an aqueous solution or crystal. Usually, tetrasodium pyrophosphate stabilizes hydrogen peroxide without changing intrinsic properties of hydrogen peroxide. In other words, it prevents the problems caused by using hydrogen peroxide alone. Decomposition of hydrogen peroxide may be promoted by metallic catalase, UV-ray, oxidase, thermal treatment, etc., whereas tetrasodium pyrophosphate peroxidate is stable against the above-described materials and treatments and displays intrinsic properties and functions of hydrogen peroxide. In practice, using tetrasodium pyrophosphate peroxidate in a liquid, gel or paste phase shows good stability with time at a temperature of 40° C., as compared to using peroxide alone. However, even though using tetrasodium pyrophosphate peroxidate, the stability of peroxide in the patch cannot easily achieved.

In general, peroxide is known to be hardly stabilized in a patch product due to its good reactivity. Further, it has poor compatibility with polymers. The stability of peroxide in products relates to a type or preparation of the products. In connection with the stability of peroxide in products, there are many patents dealing with the stabilization of peroxide in ordinary gel, paste or solution phase and some of them are found to assure a stability of certain extent at a high temperature. However, there is no suggestion with respect to the stabilization of peroxide in a thin-coated gel or patch. The present inventors likewise found after conducting many studies that such problem cannot be solved by means of known peroxide stabilizers. Now, the inventors have discovered a stabilizer, which can be used within range in application of the present invention without harming fundamental properties of the patch according to the present invention and can improve the stability with time of peroxide in the patch at a high temperature, during screening stabilizers for peroxide in the patch. Therefore, in accordance with another aspect of the present invention, a peroxide stabilizer is used together with peroxide as a teeth whitening agent.

The peroxide stabilizer having a good compatibility with the peroxide which can be used in the patch for teeth whitening of the present invention is one or more selected from the group consisting of alkylaryl sulphonates, alkyl sulphonates, alkyl carboxylates, alkyldiphenyloxide disulphonates, a series of Span such as Span 20 (sorbitan monolaurate), Span 40 (sorbitan monopalmitate), Span 60 (sorbitan monostearate), Span 80 (sorbitan monooleate) and Span 85 (sorbitan trioleate), TWEEN (POE sorbitan fatty acid ester) series. More detailed explanation for the peroxide stabilizer is explained below.

The patch for teeth whitening according to the present invention contains peroxide as a main teeth whitening agent. When the patch is manufactured using the teeth whitening agent only and then stored in 40° C., the content of the peroxide in the patch decreases as time goes by. Accordingly, the whitening effects of the patch in vitro are also observed to be lower, compared to a new patch. For a gel type formulation, loss of peroxide with time is small even when excessive polymer is used as a film former and a peroxide stabilizer is not added. Even when the preparation has low peroxide, stability, the desired effect can be obtained by using a small amount of a chelating agent, such as EDTA or sodium citrate, known as a common peroxide stabilizer. In a teeth whitening patch wherein the solvent of the gel layer is evaporated to form a sheet-shaped patch, when a stabilizer is not used in the preparation, the peroxide stability is diminished, compared to the gel type formulation. It is also observed that the addition of a chelating agent results in a decrease in the peroxide stability of the patch, compared to a patch without a chelating agent. Furthermore, even when using Dequest phosphonates, which are known for their superior peroxide stabilizing effects, suitable peroxide stabilization cannot be obtained.

As described above, the reason why the peroxide stability in the patch differs in accordance with the type of formulations such as gel, liquid or sheet may be explained in a variety of ways. According to U.S. Pat. No. 4,320,102, peroxide is described as being readily decomposed through a reaction catalyzed by a minimal amount of metal contained in the composition. There have been reported data showing that the presence of 0.1 mg of iron, 0.2 mg of copper, 0.1 mg of magnesium or 0.02 mg of chromium per one liter of a peroxide will lead to decomposition of the peroxide. A sheet-type patch formed by evaporation of the solvent in a solution-type or gel-type patch would include a high content of metal on the thin sheet of patch. Further, a sheet-type patch has a large surface area, which allows a high rate of reaction on the surface, and also lowers the stability of the peroxide.

The stabilizer contained in the patch according to the present invention is mostly a surfactant or emulsifier, which is considered to form micelles and produce preferable effects on the peroxide stabilization of the product. For example, the stabilizer prevents the contact between the peroxide and material having low compatibility with the peroxide, uniformly disperses a whitening agent in the patch when a glassy polymer having poor spreadability is used, and allows to uniformly apply an adhesive layer. In practice, it was found that when gel is applied thinly over a large surface area, the residual amount of peroxide decreases with time, while a gel of the same composition, contained in a container, is stable at a relatively high temperature. The present inventors found that since some hydrophilic glassy polymers have a good compatibility with peroxide, a solution of the hydrophilic glassy polymer with adjusted solvent ratio can sufficiently the peroxide without the use of a peroxide stabilizer. Accordingly, the present invention is not limited to a combination of peroxide and a peroxide stabilizer. Now, more detailed description is described below.

Hydrophilic glassy polymers such as polyvinyl pyrrolidone (PVP, K-15~K-120), polyquaternium-11, polyquaternium-39, polyvinyl pyrrolidone-vinyl acetate copolymer (PVP/VA copolymer) are highly compatible with peroxides and are easily soluble in water, ethanol or a mixture thereof. Accordingly, peroxide in the patch can be stabilized by using a mixture of water and ethanol in a mixing ratio of 9:1 to 0:10, without using a peroxide stabilizer. It is believed that the good compatibility of polyvinyl pyrrolidone with a peroxide results from the stabilization of peroxide by formation of a complex with polyvinyl pyrrolidone via hydrogen bonding. Polyvinyl pyrrolidone (PVP) is the most preferred hydrophilic glassy polymer to be used in the active ingredient-containing layer containing peroxide. Among the available PVP, K-15~K-120 are used, and K-90 (PVP) is preferably used in the patch of the present invention. K-30 (PVP) is more preferable since higher gel content is desired in the efficiency upon producing by a casting method. Preferably, the PVP has a relatively high molecular weight, preferably greater than about 500,000, more preferably greater than about 1,000,000. In a preferred embodiment, PVP having a molecular weight of 1,270,000 is used. Further, peroxides are found to be highly compatible with polymers having quaternary ammonium structure, such as polyquaternium. According to the present invention, a mixture of water and ethanol is used as solvent for adhesive materials. Glassy polymers which are highly compatible with peroxide are typically so hydrophilic that they cannot be uniformly coated on the surface of a release liner or other sheet. The mixture of water and ethanol can solve such problem so as to form a uniform sheet layer. Therefore, in accordance with another aspect of the present invention, there is provided a patch for tooth whitening comprising a peroxide as a tooth whitening agent and a glassy polymer having a good compatibility with the peroxide, wherein the patch is stabilized at a high temperature by adjusting the ratio of water and ethanol without addition of a peroxide stabilizer. Also, the patches of the present invention further comprise a plasticizer to provide a sufficient flexibility for the patch. Suitable plasticizer includes propylene glycol, glycerin, and polyethylene glycol although it will vary depending on the kind and preparation of the polymer used.

Further, the present invention may include a polyphosphate as a whitening aid agent other than a peroxide as a main whitening agent in order to enhance whitening effects. Polyphosphates which can be used in the present invention include one or more selected from the group consisting of tetrasodium pyrophosphate (TSPP), sodium acid pyrophosphate (SAPP), sodium hexametaphosphate (SHMP), sodium tripolyphosphate (STP), sodium potassium tripolyphosphate (SKTP), tetrapotassium pyrophosphate (TKPP), acidic sodium metapolyphosphate (Sporix) and acidic sodium polyphosphate (Multiphos). In general, it is known that polyphosphate may be used effectively as a tartar controller in toothpaste to inhibit the formation of dental calculus or to remove dental calculus. Polyphosphate is also known as a good chelating agent to enhance the teeth whitening effects to some extent since it can effectively remove stains formed on the surface of the teeth, especially those formed of metal such as iron, calcium, magnesium, etc. derived from foods or working circumstances. It has been found that polyphosphate used along with peroxide in the patch according to the present invention may inhibit scale formation and remove dental calculus by lengthening the contact time between the teeth and the polyphosphate. In practice, it is observed that when attaching the patch of the present invention to the teeth, the surface of teeth and gaps between teeth get cleaned.

Polymers which can be used in the backing layer of the matrix type patch according to the present invention include polyvinyl acetate, ethyl cellulose, polymethyl methacrylate, methacryloylethyl betain/methacrylate copolymer, commercially available under the trade name of Yukaformer manufactured by Mitsubishi, methacrylic acid copolymers, such as Eudragit L 100, Eudragit L 125, Eudragit L 100-55, Eudragit L 30D-55, aminoalkylmethacrylate copolymers, such as Eudragit E 100, Eudragit E 125, Eudragit RL 100, Eudragit RL 30D, cellulose acetate phthalate, Shellac and mixtures thereof. In addition, polymers used as enteric coating materials, which are not dissolved at pH 6 to 8 in the oral cavity, may be used.

The backing layer of the patch for teeth whitening according to the present invention may contain various plasticizers for sufficient flexibility. In this case, many kinds of plasticizer including the plasticizers described above, such as propylene glycol, glycerin, polyethylene glycol, can be used depending on the kind of the solvent used. For example, castor oil or hydrogenated castor oil may also be used.

Further, upon attaching the patch of the present invention to the teeth, in order to make the teeth visually white due to physical and chemical reactions, any white pigment may be used in the backing layer. For example, titanium dioxide, talc, hydroxyapatite, zinc oxide, or mixtures thereof may be used as the white pigment. When these pigments are not compatible with a peroxide used as a whitening agent, surface-treated titanium dioxide may be used. In addition, it is possible to employ pearl material or pigments of a variety of colors depending on individual tastes.

In accordance with the present invention, substances such as enzymes, particularly dextranase or glucose oxidase, which cannot be used in conventional toothpaste due to their instability with time, may be used alone or in a mixture. It is also possible to add papain, which is known to have teeth whitening effects. For the treatment of oral diseases, triclosan, chlorhexidin, vitamin E or its derivatives such as vitamin E acetate, oxidants effective for treating halitosis, chlorophyll or its derivatives, flavors, etc., can be used.

The method for using the patch for teeth whitening according to the present invention comprises attaching the patch to the tooth surface to be whitened. The patch consists of a water-soluble section and a water-insoluble section (backing layer). The water-soluble section is directly contacted with the surface of the teeth, and the backing layer acts as a protective wall. As the dry type patch for teeth whitening is hydrated, its flexibility and adhesive strength increase. If the tooth surface is too dry, the patch is initially not attached to the tooth surface. Since the patch can be sufficiently hydrated even in the presence of a small amount of moisture, there is no special problem so long as the tooth surface is not completely dried. In addition, since an excess of moisture can rapidly dissolve the hydrophilic glassy polymer, the adhesive strength of the patch is greatly reduced. Accordingly, it is undesirable to drink a large amount of water or beverage during wearing the patch for teeth whitening.

Specifically, first, a user places the patch on the central portion of the teeth using the fingers and closely adheres it to the tooth surface. At this time, it is preferred to use the fingers and the tongue for close adherence to the space between adjacent teeth.

The patch for teeth whitening of the present invention can be naturally detached from the teeth after attachment to the teeth for 30 minutes to 1 hour. Occasionally, the patch is not easily detached even after a fairly long period of time. However, more time is required to be naturally detached. In this case, there is no problem in terms of safety and instead teeth whitening effects are enhanced. If desired, the wearer may easily detach the patch using water.

Since the patch for teeth whitening of the present invention ensures the sufficient contact between the peroxide and tooth stains for a desired time, it is effective for teeth whitening effects but does not sufficiently provide a refreshing feeling to the wearer as toothpastes does. For this reason, the wearer can brush his teeth after detaching the patch. However, brushing before attachment to the patch is not recommended because it may cause irritation to the teeth.

COMPARATIVE EXAMPLES

Hereinafter, the present invention will be described in more detail with reference to the following examples. However, these examples are given for the purpose of illustration and are not to be construed as limiting the scope of the invention.

Examples 1 to 5, Comparative Example 1

In accordance with the compositions described below, patches for teeth whitening of Examples 1 to 5 and Comparative Example were manufactured.

Example 1

Solution for Preparing Active Material-Containing Adhesive Layer

Water was added to a mixture of 10% of polyvinyl alcohol, 10% of polyvinyl pyrrolidone, 5% of tetrasodium pyrophosphate peroxidate, 2% of alkylaryl sulfonate (SLS) and 3% of glycerin until the total amount reached 100%.

Solution for Preparing Backing Layer

Ethanol was added to a mixture of 8% of ethyl cellulose, 5% of Eudragit and 4% of castor oil until the total amount reached 100%.

Example 2

Solution for Preparing Adhesive Layer

Ethanol was added to 30% of hydroxypropyl cellulose until the total amount reached 100%.

Solution for Preparing Active Material-Containing Layer

Water was added to a mixture of 20% of polyvinyl pyrrolidone, 5% of hydrogen peroxide, 10% of glycerin and 30% of ethanol until the total amount reached 100%.

Solution for Preparing Backing Layer

Ethanol was added to a mixture of 5% of polyvinyl acetate, 5% of Yukaformer (Mitsubishi) and 6% of glycerin until the total amount reached 100%.

Example 3

Solution for Preparing Active Material-Containing Adhesive Layer

Water was added to a mixture of 10% of polyquaternium-39, 10% of carbamide peroxide and 50% of ethanol until the total amount reached 100%.

Solution for Preparing Backing Layer

A mixed solvent (acetone/ethanol=4/1) was added to a mixture of 30% of cellulose acetate phthalate and 4% of castor oil until the total amount reached 100%.

Example 4

Solution for Preparing Adhesive Layer

Ethanol was added to 20% of polyvinyl pyrrolidone until the total amount reached 100%.

Solution for Preparing Active Material-Containing Layer

Water was added to a mixture of 12% of polyalkylvinyl ether-maleic acid copolymer (Grantrez S 97) and 6% of tetrasodium pyrophosphate peroxidate and 0.5% of sorbitan oleate until the total amount reached 100%.

Solution for Preparing Backing Layer

Ethanol was added to a mixture of 10%/o of ethyl cellulose and 6% of castor oil until the total amount reached 100%.

Example 5

Solution for Preparing Adhesive Layer

Water was added to 10% of polyvinyl alcohol, 10% of polyvinyl pyrrolidone and 3% of glycerin until the total amount reached 100%.

Solution for Preparing Active Material-Containing Layer

Water was added to a mixture of 20% of polyquaternium-11, 4% of PC, 4% of TKPP and 2% of sorbitan monolaurate until the total amount reached 100%.

Solution for Preparing Backing Layer

Ethanol was added to a mixture of 15% of Eudragit and 5% of propyleneglycol until the total amount reached 100%.

Comparative Example 1

Gel for Preparing Active Material-Containing Adhesive Layer

Water was added to a mixture of 12% of Carbopol, 4.5% of hydrogen peroxide, 0.48% of SAPP and 80% of glycerin until the total amount reached 100%.

Backing Layer

Polyethylene Strip

Abbreviations used above have the following meanings.

TKPP; tetrapotassium pyrophosphate, SAPP; sodium acid pyrophosphate, TSPP; tetrasodium pyrophosphate Experimental Example 1

Evaluation of Irritation to Gums

Figure 1A:
FIG. 1a is a plan view showing a Crest Whitestrip (P&G) for upper teeth.
Figure 1B:
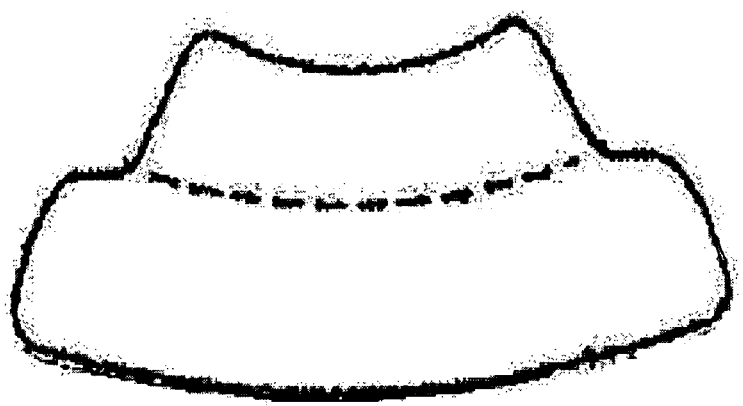

Referring to FIGS. 2a, 3a, 4a, 5a and 6a, contact areas are shown for patched for upper teeth. The patches were manufactured using the respective preparations obtained in Example 1. Contact area 100 shown in FIG. 2a has no folded portion shown, contact area 100 shown in FIG. 4a has folded portions shown but no cut line 150, and FIGS. 5a and 6a have folded portions and cut lines 150. FIG. 1a is a strip for upper teeth of Crest Whitestrip (P&G, U.S), respectively. The strip shown in FIG. 1a was manufactured using the respective preparations obtained in Comparative Example 1. As shown in FIG. 1a, the strip has folded portions and is a linear shape.

The degree of irritation to gums and wearability of the patches thus manufactured were measured after wearing the patches for 30 minutes twice daily over 2 weeks. In addition, adhesion maintenance was measured after attaching the patches to the teeth for 1 hour. The above characteristics of the patches were scored based on the following criteria. 5: very satisfied (no irritation, very strong adhesion to the teeth, fairly excellent adhesion maintenance), 4: satisfied (no or little irritation, the strong adhesion to the teeth, excellent adhesion maintenance), 3: average (slight irritation, average adhesion to the teeth, average adhesion maintenance), 2: unsatisfied (irritation at initial stage, weak adhesion to the teeth, poor adhesion maintenance), and 1: very unsatisfied (continuous irritation in use, very weak adhesion to the teeth, very poor adhesion maintenance).

The patches shown in FIGS. 1a, 2a, 3a, 4a, 5a and 6a had a length sufficient to cover six to eight teeth. The degree of irritation to the gums, wearability and adhesion maintenance of the patches were measured on ten people, respectively. The results are shown in Table 1.

TABLE 1

| | Degree of irritation to gums | Wearability | Adhesive strength to teeth | Adhesion maintenance |
|---|---|---|---|---|
| FIG. 2a | 4.5 | 4 | 5 | 3 |
| FIG. 3a | 4 | 3 | 4 | 5 |
| FIG. 4a | 4 | 4 | 4 | 5 |
| FIG. 5a | 4 | 4 | 4 | 5 |
| FIG. 6a | 4 | 4 | 4 | 5 |
| FIG. 1a | 3 | 3 | 3 | 2 |

As can be from Table 1, although the patches shown in FIGS. 2a, 3a, 4a, 5a and 6a were manufactured using the preparations of Example 1, the unfolded type patch of FIG. 2a was most excellent in the measurement of irritation to gums (e.g. the least irritation) and the folded type patches of FIGS. 3a, 4a, 5a and 6a were excellent in the measurement of adhesion maintenance, compared to the unfolded type patch of FIG. 2a. Accordingly, it is estimated that when wearing for thirty minutes or longer, a folded type patch is preferred. In conclusion, the degree of irritation to gums, wearability and adhesion maintenance of a patch depend on the type (wet or dry) of the patch. The physical properties of a dry type patch depend on the shape (folded or unfolded) of the dry type patch.

Experimental Example 2

The adhesive strength of the patches for teeth whitening to the teeth was measured according to the following mechanical method.

(1) Preparation of Hydroxyapatite (HAP) Tablet Specimen

Hydroxyapatite powder was formed into a tablet by means of an IR press. The resulting tablet was sintered at a temperature of 1000° C.

(2) Evaluation of Adhesive Strength to Teeth

The adhesive strength of the patches to hydroxylapatite as an artificial tooth material was measured using a miniature tensile tester. The results are shown in Table 2 below. The adhesive strength in a dry state was measured after completely drying the sintered hydroxyapatite specimen. The adhesive strength in a wet state was measured after sufficiently adding water to the sintered hydroxyapatite specimen until the specimen was completely wetted and then removing moisture on the surface of the specimen. The wetting conditions were set because the oral cavity is humid but the tooth surface is not wet enough to discover moisture. The adhesive strength of the patches to teeth was obtained by pressurizing the patches to the specimens at a constant force for a constant time and measuring a force required for detaching the attached patches. The measurement was repeated several times. The results are shown in Table 2.

TABLE 2

| | Adhesive strength in dry state | Adhesive strength in wet state |
|---|---|---|
| Example 1 | 0.8 | 205.9 |
| Example 2 | 24.3 | 85.75 |
| Example 3 | 40.0 | 105.5 |
| Example 4 | 17.0 | 160.2 |
| Example 5 | 22.1 | 114.0 |
| Comparative Example 1 | 38.0 | 39.5 |

As can be seen from Table 2, the dry type patches of Examples 1 to 5 showed 2~260 times higher adhesive strength in a dry state than in a wet state. On the other hand, there was no significant difference between the adhesive strength of the wet type patch, which is a strip on which gel was coated, of Comparative Example 1 in a wet state and a dry state.

As apparent from the above description, the patch for teeth whitening according to the present invention is a dry type patch in which a hydrophilic glassy polymer is used as a material for layers other than a backing layer. After the dry type patch is attached to the teeth, the glassy polymer provides strong adhesion to the teeth while being hydrated by moisture on the tooth surface and a whitening agent begins to be released. Accordingly, the dry type patch is a safe formulation having no problem in use. In addition, although the dry type patch comes into contact with the hands or other sites, it does not leave any residue, which provides convenience in use. Further, since the dry type patch has a high adhesion to the teeth, it is not detached from the teeth during being worn and thus exhibits excellent whitening effects. Furthermore, since contact surface 100 of dry type patch covers all the portions of the teeth while minimizing contact with gums, no or little irritation is caused and wearability is excellent.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A tooth whitening patch comprising a combination formed from the following materials:
   (1) a peroxide,
   (2) polyvinyl pyrrolidone and/or polyvinyl alcohol,
   (3) hydroxypropylmethyl cellulose, polyalkylvinyl ether-maleic acid copolymer and/or polyquaternium-39
   (4) a polyphosphate,
wherein the patch has adhesive strength, and wherein the adhesive strength of the patch will increase upon becoming hydrated by applying the patch to a user's teeth by at least 1.6 time to 25,712 times post hydration.

2. The patch of claim 1, wherein the adhesive strength of the patch, upon becoming hydrated, at least doubles as compared to before becoming hydrated.

3. The patch of claim 1, wherein the patch comprises two layers and one of the layers is the layer which provides the adhesive strength of the patch.

4. The patch of claim 3, wherein the other layer is a backing layer.

5. The patch of claim 3, wherein the layer with adhesive strength comprises a combination formed from hydrogen peroxide and polyvinyl pyrrolidone.

6. The patch of claim 5, wherein the other layer is a backing layer.

7. The patch of claim 5, wherein the hydrogen peroxide and polyvinyl pyrrolidone form a complex via hydrogen bonding.

8. The patch of claim 1, wherein the combination further comprises one or more plasticizers.

9. The patch of claim 8, wherein the plasticizers are selected from the group consisting of propylene glycol and glycerin.

10. The patch of claim 1, wherein the combination further comprises a stabilizer for hydrogen peroxide.

11. The patch of claim 1, wherein the adhesive strength of the patch, upon becoming hydrated, fixes the patch to the user's teeth.

12. The patch of claim 11, wherein the fixed patch has sufficient contact time with the user's teeth to allow the patch to whiten the user's teeth.

13. A tooth whitening patch comprising a combination formed from the following materials:
 (1) hydrogen peroxide,
 (2) polyvinyl pyrrolidone, as an adhesive polymer and
 (3) sodium tetrapyrophosphate,
wherein the patch has adhesive strength, and the adhesive strength of the patch will increase upon becoming hydrated by applying the patch to a user's teeth by at least 1.6 time to 25,712 times post hydration.

14. The patch of claim 13, wherein the adhesive strength of the patch, upon becoming hydrated, at least doubles as compared to before becoming hydrated.

15. The patch of claim 13, wherein the patch comprises two layers and one of the layers is the layer which provides the adhesive strength of the patch.

16. The patch of claim 15, wherein the other layer is a backing layer.

17. The patch of claim 15, wherein the layer with adhesive strength comprises a combination formed from hydrogen peroxide and polyvinyl pyrrolidone.

18. The patch of claim 17, wherein the other layer is a backing layer.

19. The patch of claim 17, wherein the hydrogen peroxide and polyvinyl pyrrolidone form a complex via hydrogen bonding.

20. The patch of claim 17, wherein the combination further comprises sodium tripolyphosphate.

21. The patch of claim 13, wherein the combination further comprises hydroxypropylmethyl cellulose.

22. The patch of claim 13, wherein the combination further comprises one or more plasticizers.

23. The patch of claim 22, wherein the plasticizers are selected from the group consisting of propylene glycol and glycerin.

24. The patch of claim 13, wherein the combination further comprises a stabilizer for hydrogen peroxide.

25. The patch of claim 13, wherein the adhesive strength of the patch, upon becoming hydrated, fixes the patch to the user's teeth.

26. The patch of claim 25, wherein the fixed patch has sufficient contact time with the user's teeth to allow the patch to whiten the user's teeth.

27. An active ingredient-containing adhesive layer for application to teeth comprising a combination formed from:
 (1) hydrogen peroxide,
 (2) polyvinyl pyrrolidone, as an adhesive polymer and
 (3) a polyphosphate,
and wherein the adhesive strength of the adhesive layer will increase upon becoming hydrated by applying the adhesive layer to a user's teeth by at least 1.6 time to 25,712 times post hydration.

28. The adhesive layer of claim 27, wherein the polyphosphate is selected from the group consisting of tetrasodium pyrophosphate, sodium acid pyrophosphate, sodium hexametaphosphate, sodium hexametaphosphate, sodium tripolyphosphate, sodium potassium tripolyphosphate, tetrapotassium pyrophosphate, acidic sodium metapolyphosphate and combinations thereof.

29. The adhesive layer of claim 27, wherein the polyphosphate is sodium tripolyphosphate.

30. A tooth whitening patch comprising two layers, wherein one of the layers is an active ingredient-containing adhesive layer for application to teeth comprising a combination formed from:
 (1) hydrogen peroxide, and
 (2) polyvinyl pyrrolidone, as an adhesive polymer
wherein the adhesive layer has adhesive strength, wherein the adhesive strength of the adhesive layer will increase upon becoming hydrated by applying the adhesive layer to a user's teeth by at least 1.6 time to 25,712 times post hydration, and wherein one of the layers comprises sodium tripolyphosphate.

31. A tooth whitening patch comprising two layers, wherein one of the layers is an active ingredient-containing adhesive layer for application to teeth comprising a combination formed from:
 (1) hydrogen peroxide, and
 (2) polyvinyl pyrrolidone, as an adhesive polymer
wherein the adhesive layer has adhesive strength, wherein the adhesive strength of the adhesive layer will increase upon becoming hydrated by applying the adhesive layer to a user's teeth by at least 1.6 time to 25,712 times post hydration, and wherein the adhesive layer comprises sodium tripolyphosphate.

* * * * *

UNITED STATES PATENT AND TRADEMARK OFFICE
CERTIFICATE OF CORRECTION

| | | |
|---|---|---|
| PATENT NO. | : 8,652,446 B2 | Page 1 of 1 |
| APPLICATION NO. | : 10/717226 | |
| DATED | : February 18, 2014 | |
| INVENTOR(S) | : Kim et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,005 days.

Signed and Sealed this
First Day of December, 2015

Michelle K. Lee
*Director of the United States Patent and Trademark Office*